(12) United States Patent
Fernandez et al.

(10) Patent No.: US 10,820,916 B2
(45) Date of Patent: Nov. 3, 2020

(54) COPLANAR X-RAY GUIDED AIMING ARM FOR LOCKING OF INTRAMEDULLARY NAILS

(71) Applicant: DePuy Synthes Products, Inc., Raynham, MA (US)

(72) Inventors: Alberto Fernandez, Montevideo (UY); Markus Buettler, Oensingen (CH); Andreas Waelchli, Vettligen (CH)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 16/128,173

(22) Filed: Sep. 11, 2018

(65) Prior Publication Data

US 2019/0015114 A1 Jan. 17, 2019

Related U.S. Application Data

(63) Continuation of application No. 12/984,974, filed on Jan. 5, 2011, now Pat. No. 10,080,574, which is a (Continued)

(51) Int. Cl.
*A61B 17/17* (2006.01)
*A61B 90/00* (2016.01)
*A61B 17/00* (2006.01)

(52) U.S. Cl.
CPC ...... *A61B 17/1725* (2013.01); *A61B 17/1703* (2013.01); *A61B 90/39* (2016.02); (Continued)

(58) Field of Classification Search
CPC .. A61B 17/1725; A61B 17/1703; A61B 90/39
See application file for complete search history.

(56) References Cited

U.S. PATENT DOCUMENTS 2,531,734 A 11/1950 Hopkins
3,613,684 A 10/1971 Sheridan
(Continued)

FOREIGN PATENT DOCUMENTS

CH 664725 3/1988
CH 668692 1/1989
(Continued)

*Primary Examiner* — Ellen C Hammond
(74) *Attorney, Agent, or Firm* — Fay Kaplun & Marcin, LLP

(57) ABSTRACT

A novel coplanar X-ray guided method and device for insertion of distal locking screws in intramedullary bone nails. The device has coplanar holes, which allow insertion of protective sleeves. A drill and bone screws can be inserted through the protective sleeves. Radiopaque target markers in the aiming arm enable the easy positioning of an X-ray source such that an X-ray beam is coplanar with the aiming arm transverse holes. After the X-ray source is accurately oriented, a single X-ray snapshot is enough to assess the exact distortion of the implanted intramedullary nail. The X-ray beam need not be coaxial with the intramedullary nail holes. The aiming arm has a mobile portion and a fixed portion fastened to the nail, wherein said aiming arm can be adjusted, displacing the mobile portion over the fixed portion, to compensate for the distortion of the intramedullary nail after implantation. Once the aiming arm is precisely positioned, the aiming arm transverse holes and intramedullary nail holes are accurately aligned, protective sleeves are inserted through aiming arm holes, bone drills are drilled through the intramedullary nail holes and surrounding bone material, and bone screws are inserted, locking the intramedullary nail to the bone.

20 Claims, 17 Drawing Sheets

Related U.S. Application Data continuation of application No. 11/240,785, filed on Sep. 23, 2005, now Pat. No. 7,887,545, which is a continuation-in-part of application No. 10/947,155, filed on Sep. 23, 2004, now Pat. No. 7,481,815.

(52) U.S. Cl.
CPC .............. *A61B 2017/00831* (2013.01); *A61B 2017/00915* (2013.01)

(56) References Cited

U.S. PATENT DOCUMENTS

| | | |
|---|---|---|
| 3,704,707 A | 12/1972 | Halloran |
| 4,037,592 A | 7/1977 | Kronner |
| 4,418,422 A | 11/1983 | Richter et al. |
| 4,541,424 A | 9/1985 | Grosse et al. |
| 4,621,628 A | 11/1986 | Brudermann |
| 4,622,959 A | 11/1986 | Marcus |
| 4,625,718 A | 12/1986 | Olerud et al. |
| 4,667,664 A | 5/1987 | Taylor et al. |
| 4,722,336 A | 2/1988 | Kim et al. |
| 4,803,976 A | 2/1989 | Frigg et al. |
| 4,848,327 A | 7/1989 | Perdue |
| 4,850,344 A | 7/1989 | Olerud et al. |
| 4,865,025 A | 9/1989 | Buzzi et al. |
| 4,877,019 A | 10/1989 | Vives |
| 4,881,535 A | 11/1989 | Sohngen |
| 4,917,111 A | 4/1990 | Pennig et al. |
| 4,969,889 A | 11/1990 | Greig |
| 4,976,713 A | 12/1990 | Landanger et al. |
| 5,013,317 A | 5/1991 | Cole et al. |
| 5,030,222 A | 7/1991 | Calandruccio et al. |
| 5,031,203 A | 7/1991 | Trecha |
| 5,070,861 A | 12/1991 | Einars et al. |
| 5,112,336 A | 5/1992 | Krevolin et al. |
| 5,127,913 A | 7/1992 | Thomas, Jr. |
| 5,234,434 A | 8/1993 | Goble et al. |
| 5,261,915 A | 11/1993 | Durlacher et al. |
| 5,283,808 A | 2/1994 | Cramer et al. |
| 5,295,991 A | 3/1994 | Frigg |
| 5,306,278 A | 4/1994 | Dahl et al. |
| 5,308,350 A | 5/1994 | Mikhail |
| 5,312,412 A | 5/1994 | Whipple |
| 5,334,192 A | 8/1994 | Behrens |
| 5,334,203 A | 8/1994 | Wagner |
| 5,346,496 A | 9/1994 | Pennig |
| 5,352,228 A | 10/1994 | Kummer et al. |
| 5,403,320 A | 4/1995 | Luman et al. |
| 5,403,321 A | 4/1995 | DiMarco |
| 5,403,322 A | 4/1995 | Herzenberg et al. |
| 5,411,503 A | 5/1995 | Hollstien et al. |
| 5,417,688 A | 5/1995 | Elstrom et al. |
| 5,426,687 A | 6/1995 | Goodall et al. |
| 5,429,641 A | 7/1995 | Gotfried |
| 5,433,720 A | 7/1995 | Faccioli et al. |
| 5,458,600 A | 10/1995 | Stapert et al. |
| 5,470,335 A | 11/1995 | Du Toit |
| 5,474,561 A | 12/1995 | Yao |
| 5,478,329 A | 12/1995 | Ternamian |
| 5,478,343 A | 12/1995 | Ritter |
| 5,489,284 A | 2/1996 | James et al. |
| 5,498,265 A | 3/1996 | Asnis et al. |
| 5,499,986 A | 3/1996 | Dimarco |
| 5,513,240 A | 4/1996 | Hausmann et al. |
| 5,514,145 A | 5/1996 | Durham et al. |
| 5,540,691 A | 7/1996 | Elstrom et al. |
| 5,569,262 A | 10/1996 | Carney |
| 5,576,194 A | 11/1996 | Chan |
| 5,584,838 A | 12/1996 | Rona et al. |
| 5,613,971 A | 3/1997 | Lower et al. |
| 5,620,449 A | 4/1997 | Faccioli et al. |
| 5,624,447 A | 4/1997 | Myers |
| 5,630,805 A | 5/1997 | Ternamian |
| 5,665,086 A | 9/1997 | Itoman et al. |
| 5,681,318 A | 10/1997 | Pennig et al. |
| 5,707,375 A | 1/1998 | Durham et al. |
| 5,722,978 A | 3/1998 | Jenkins, Jr. |
| 5,728,128 A | 3/1998 | Crickenberger et al. |
| 5,766,179 A | 6/1998 | Faccioli et al. |
| 5,772,594 A | 6/1998 | Barrick |
| 5,855,579 A | 1/1999 | James et al. |
| 5,891,158 A | 4/1999 | Manwaring |
| 5,899,908 A | 5/1999 | Kuslich et al. |
| 5,904,685 A | 5/1999 | Walawalkar |
| 5,913,860 A | 6/1999 | Scholl |
| 5,951,561 A | 9/1999 | Pepper et al. |
| 5,989,260 A | 11/1999 | Yao |
| 6,015,408 A | 1/2000 | Pichon et al. |
| 6,024,746 A | 2/2000 | Katz |
| 6,027,506 A | 2/2000 | Faccioli et al. |
| 6,027,507 A | 2/2000 | Anderson et al. |
| 6,033,407 A | 3/2000 | Behrens |
| 6,036,657 A | 3/2000 | Milliman et al. |
| 6,036,696 A | 3/2000 | Lambrecht et al. |
| 6,080,159 A | 6/2000 | Vichard |
| 6,126,659 A | 10/2000 | Wack |
| 6,126,661 A | 10/2000 | Faccioli et al. |
| 6,129,729 A | 10/2000 | Snyder |
| 6,168,595 B1 | 1/2001 | Durham et al. |
| 6,174,335 B1 | 1/2001 | Varieur et al. |
| 6,183,477 B1 | 2/2001 | Pepper |
| 6,214,013 B1 | 4/2001 | Lambrecht et al. |
| 6,371,959 B1 | 4/2002 | Trice |
| 6,514,253 B1 | 2/2003 | Yao |
| 6,635,061 B1 | 10/2003 | Snyder |
| 6,656,189 B1 | 12/2003 | Wilson et al. |
| 6,702,823 B2 | 3/2004 | Iaia |
| 7,056,322 B2 | 6/2006 | Davison et al. |
| 7,175,633 B2 | 2/2007 | Roth et al. |
| 8,591,517 B2 | 11/2013 | Metzinger et al. |
| 8,675,930 B2 | 3/2014 | Funk et al. |
| 8,685,034 B2 | 4/2014 | Giersch et al. |
| 2006/0098851 A1 | 5/2006 | Shoham et al. |

FOREIGN PATENT DOCUMENTS

| | | |
|---|---|---|
| CN | 1084382 | 3/1994 |
| EP | 0589592 | 10/1994 |
| EP | 0923906 | 11/1998 |
| WO | 92/01422 | 6/1992 |
| WO | 95/30378 | 11/1995 |
| WO | 03/92515 | 11/2003 |

COPLANAR X-RAY GUIDED AIMING ARM FOR LOCKING OF INTRAMEDULLARY NAILS

RELATED APPLICATION DATA

The present application is a Continuation of U.S. patent application Ser. No. 12/984,974 filed on Jan. 5, 2011, now U.S. Pat. No. 10,080,574; which is a Continuation of U.S. patent application Ser. No. 11/240,785 filed Sep. 23, 2005, now U.S. Pat. No. 7,887,545; which is a Continuation-in-Part of U.S. patent application Ser. No. 10/947,155 filed Sep. 23, 2004, now U.S. Pat. No. 7,481,815. The entire disclosures of the above patent(s)/application(s) are expressly incorporated herein by reference.

FIELD OF INVENTION

The present invention is directed to aiming arm locking of intramedullary nails, and in particular to X-ray guided aiming arm locking of intramedullary nails.

BACKGROUND OF THE INVENTION

It is well known the use of intramedullary nails to treat bone fractures in tubular bones. A nail is implanted in the medullary canal of the bone across the fracture site in order to retain the bone fragments on the bone nail and to secure the bone fragments from being displaced. The nail has transverse holes and is fixed to the bone by a number of locking screws or fixation bolts which must pass through holes in the nail and into the surrounding bone material. After the nail is inserted into the medullary canal, the distal end of the nail is invisible to the naked eye. Numerous methods and apparatus have been developed to successfully place locking screws across both a fractured bone and an implanted intramedullary nail.

Usually nails are locked at both ends, close to the entry point and far away from the entry point. The region of the bone where the nail is implanted is identified as proximal and the opposite end of the intramedullary nail is distal. Nail locking is currently made using either mechanical aiming arms or X-ray guidance.

Mechanical aiming instruments, which are fixedly attached to the proximal end of the implanted bone nail, may provide concentric alignment with the proximal screw holes in order to enable reliable drilling such as those disclosed in U.S. Pat. Nos. 5,334,192, 5,766,179, and 6,514,253.

An advantage of this mechanical aiming arm is that neither the patient nor the surgeon will be exposed to the X-ray source. However, distal screw holes may not perform satisfactorily due to distortion of the intramedullary nail while being driven into the bone and/or mechanical stress on the aiming arm. Aiming-arm-guided-locking is usually successful for proximal locking since the distortion of the nail when inserted into the bone is negligible for a short length of nail. However, it is usually not successful for distal locking except for very short nails since the distortion of the nail when inserted into the bone is not negligible.

Distortion in the implanted intramedullary nail happens in the 3D space and can be analyzed into its main components:
Length variation in the axis of the intramedullary nail.
Rotational distortion in the axis of the intramedullary nail.
Flexion distortion in the plane of the intramedullary nail distal holes
Flexion distortion perpendicular to the plane of the distal holes of the intramedullary nail.

We can accept, when using non slotted intramedullary nails provided of coplanar distal holes, that the first three mentioned distortions: (1) length distortion in the axis of the nail, (2) rotational distortion in the axis of the nail, and (3) flexion deformity in the plane of the distal screw holes of the nail, are negligible for our task of distal locking. However, flexion distortion in a plane perpendicular to the plane of the distal screw holes of the nail is very important and the distortion of concern when distal locking is the objective.

X-ray guidance is what is presently most used for distal locking except for very short nails. The procedure starts by exactly positioning the X-ray beam in the axis of the nail holes, something that is not always straightforward for the X-ray technician. The intramedullary nail will cast a dark, elongate image on the X-ray monitor, while the nail holes will appear as light circles or ovals. In particular, the nail hole will appear as a circle when the X-ray source is positioned such that the X-ray beam is parallel to the axis of the nail hole, something that is a complex 3D procedure.

After the nail holes have been located, a drill is used to drill through the bone for insertion of the locking screw. This procedure may be accomplished either with or without the use of an aiming arm guide, wherein said aiming arm guide can be fastened to the bone nail or not.

Various aiming guides are already known in the art to be used in conjunction with the X-ray source in order to accurately place the locking bone screws across both a fractured bone and an implanted intramedullary nail, such as those disclosed in U.S. Pat. Nos. 4,803,976, 4,850,344, 6,656,189, 4,667,664, and 4,881,535.

All these X-ray guided procedures require the X-ray source positioned such that the X-ray beam is parallel to the axis of the nail hole. This is not always simple, and sometimes not even possible. It may also increase undesirable X-ray exposure to the surgeon, patient and operating room staff, and lengthen the surgical procedure.

Attempts have been made in the past to obtain a successful method for distal locking, which overcome the problems associated with X-ray guided locking. However, most of these systems are cumbersome and require additional bone screw holes in order to exactly assess the position of the hole in the distorted intramedullary nail after implantation into the bone.

The present invention relates to a novel apparatus and method of distal locking that allows the surgeon to target and install bone screws into an intramedullary nail in an accurate, fast and reliable manner.

SUMMARY OF THE INVENTION

It is therefore an object of the present invention to provide an aiming arm capable of being adjusted to compensate for the intramedullary nail distortion after its insertion into the bone, making use of the information given by a few snap shots of the X-ray image intensifier.

Another object of the present invention is to provide a radiolucent aiming arm for distal locking of an intramedullary nail having radiopaque target markers for use in determining when the position of an X ray source is such that an X ray beam is coplanar with the aiming arm holes axis.

Further, it is an object of the present invention to reduce undesirable X-ray exposure to the surgeon, patient and operating room staff.

The present invention provides an easy and straightforward procedure for the X-ray technician and the surgeon and makes distal bone fixation of intramedullary nails simple and fast, thereby addressing one of the most important issues in actual surgery—time shortening.

The aiming arm of the present invention overcomes the disadvantages of conventional aiming arms by providing an easily obtainable X-ray guidance for distal locking without requiring that the X-ray beam be coaxial with the nail hole, thus reducing undesirable X-ray exposure to the surgeon, patient and operating room staff.

The novel feature of the present invention is an aiming arm capable of being adjusted to compensate for the nail deformation after its insertion into bone, making use of the information given by a few snap shots of the X-ray image intensifier.

By fulfilling the objectives mentioned above, the present invention is extremely helpful to the medical care area.

The preferred embodiment of the present invention provides an adjustable aiming arm fastened to a bone nail. The aiming arm is constructed of a radiolucent material and has coplanar transverse holes or apertures. The aiming arm has a number of radiopaque target markers to enable the X-ray technician to assess when the position of an X-ray source is such that an X-ray beam is coplanar with the transverse holes of aiming arm. The image shown by a single X-ray snapshot in this position gives the surgeon precise information on the amount of nail distortion after nail insertion into the bone, thereby allowing the surgeon to determine the aiming arm adjustment needed to compensate for the distortion of the intramedullary nail. Once the aiming arm is accurately oriented over the nail hole, so that the aiming arm transverse holes are coaxial with the nail holes, the surrounding bone material can be drilled. After the bone is drilled, locking bone screws are screwed through the protective sleeves previously inserted into the aiming arm transverse holes.

Other objects, advantages and novel features of the present invention will become apparent from the following detailed description of the invention when considered in conjunction with the accompanying drawings.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Hereinafter, a method of bone fixation according to the preferred embodiment of the present invention will be explained with reference to FIGS. 1-7.

Figure 1:
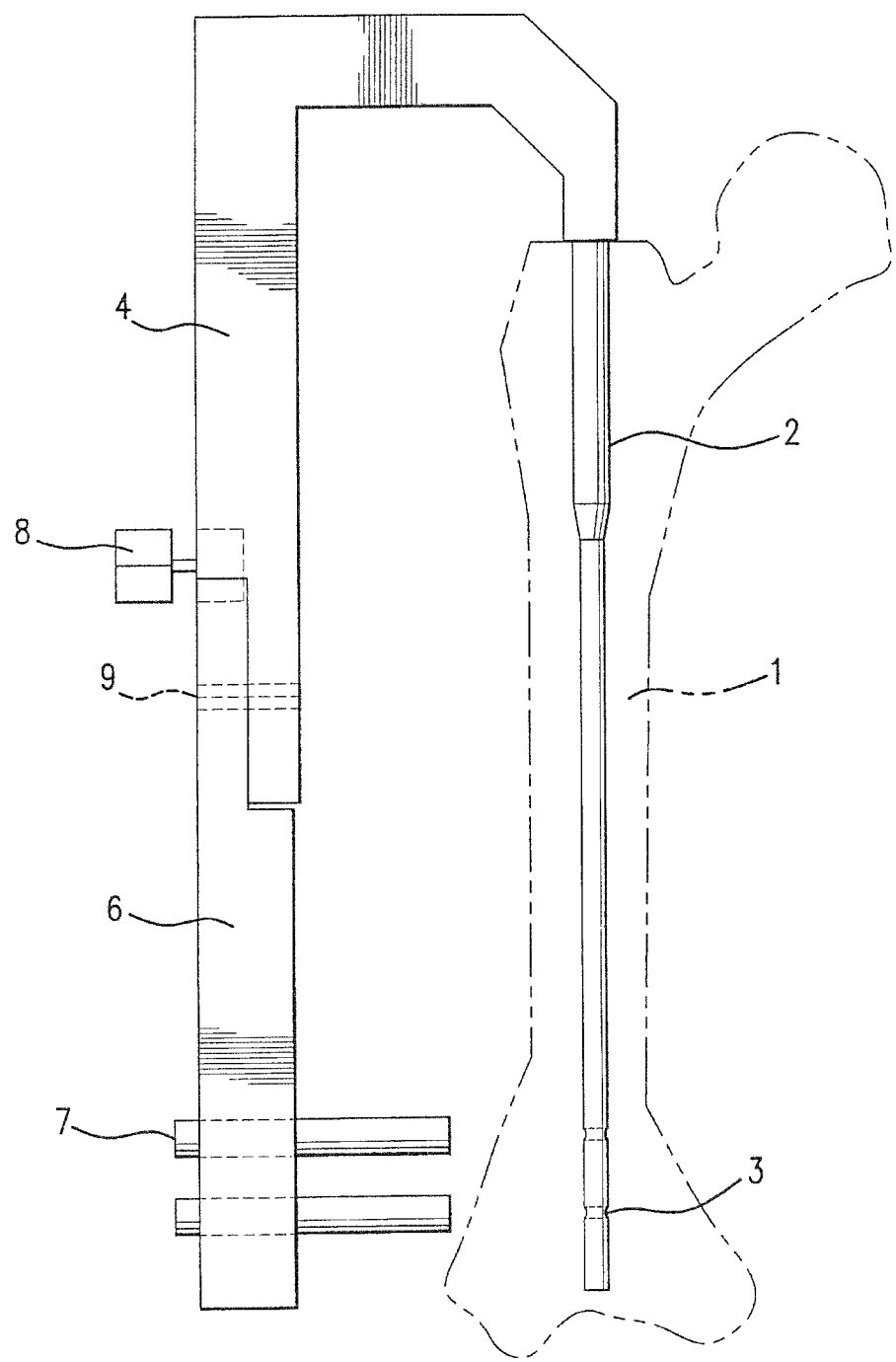
FIG. 1 shows a plan view of an aiming arm according to a preferred embodiment of the present invention wherein the protective sleeves and a fastened intramedullary nail are shown.

Referring to FIG. 1 there is shown an aiming device 4, on which is mounted a mobile aiming arm portion 6. An intramedullary nail 2, with two coplanar transverse holes 3 is fastened to the aiming arm 4. Protective sleeves 7 slide through holes 5 located in the mobile part of the aiming arm 6, guiding drills and bone screws through the nail transverse holes 3 for distal locking of the intramedullary nail 2. Mobile aiming arm portion 6 rotates about the axis 9 with respect to aiming arm 4.

Figure 2:
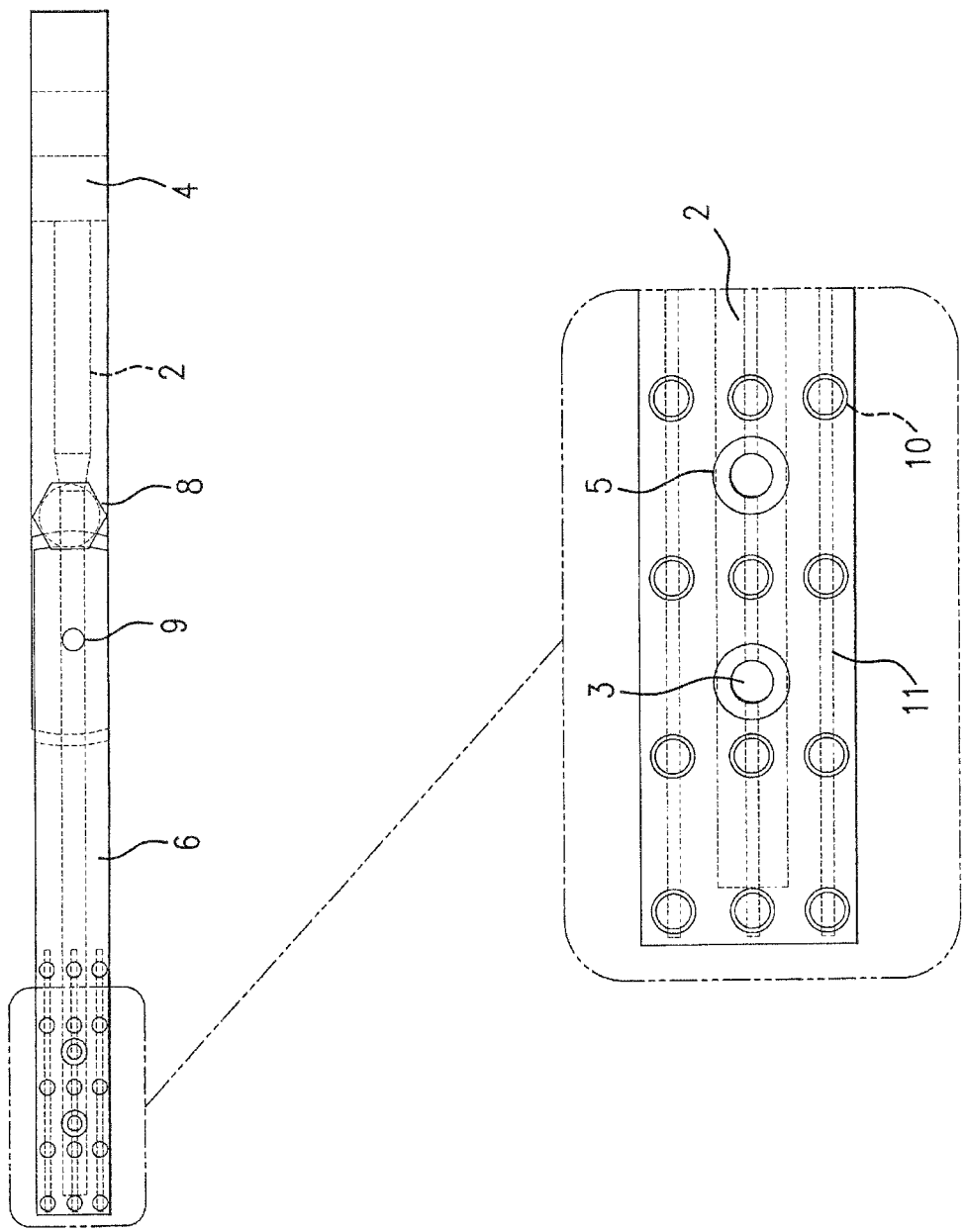
FIG. 2 is a side view illustrating the aiming arm transverse holes precisely aligned with the intramedullary nail holes.
Figure 3:
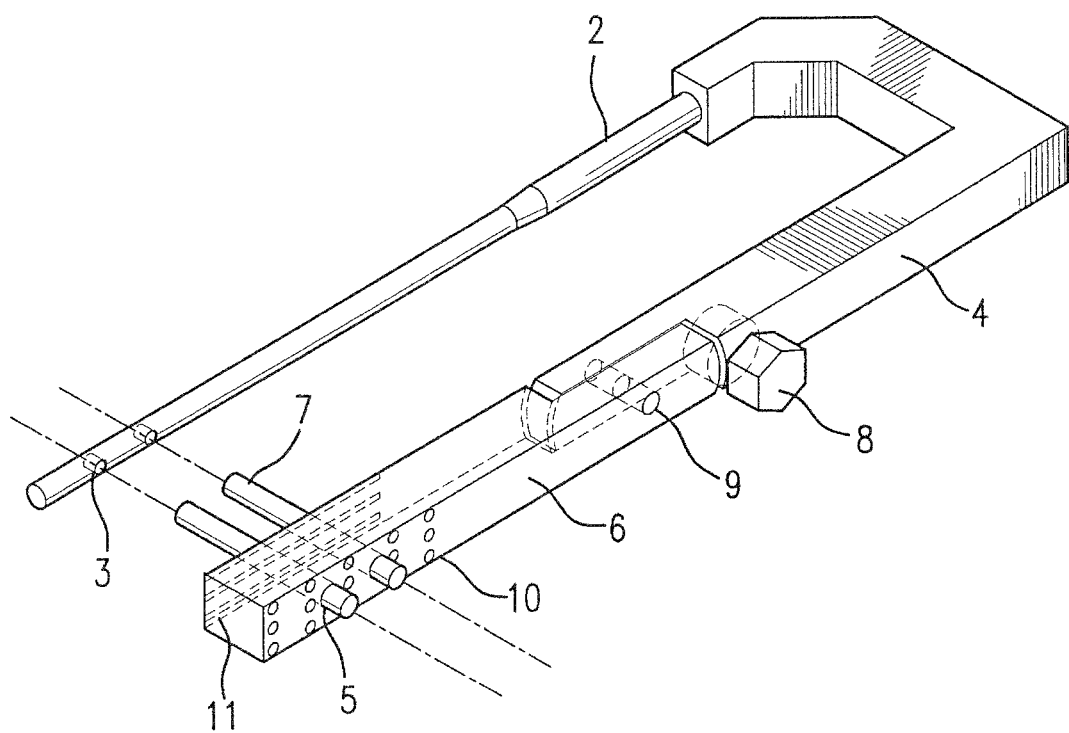
FIG. 3 shows a perspective view of the aligned aiming arm according to a preferred embodiment of the present invention, wherein the protective sleeves and the intramedullary nail fastened to the aiming arm are shown.

The aiming arm 4 is fastened to the intramedullary nail 2, and before the nail 2 is inserted into the bone 1, aiming arm holes 5 and intramedullary nail holes 3 are precisely aligned as shown in FIGS. 2 and 3.

Figure 4:
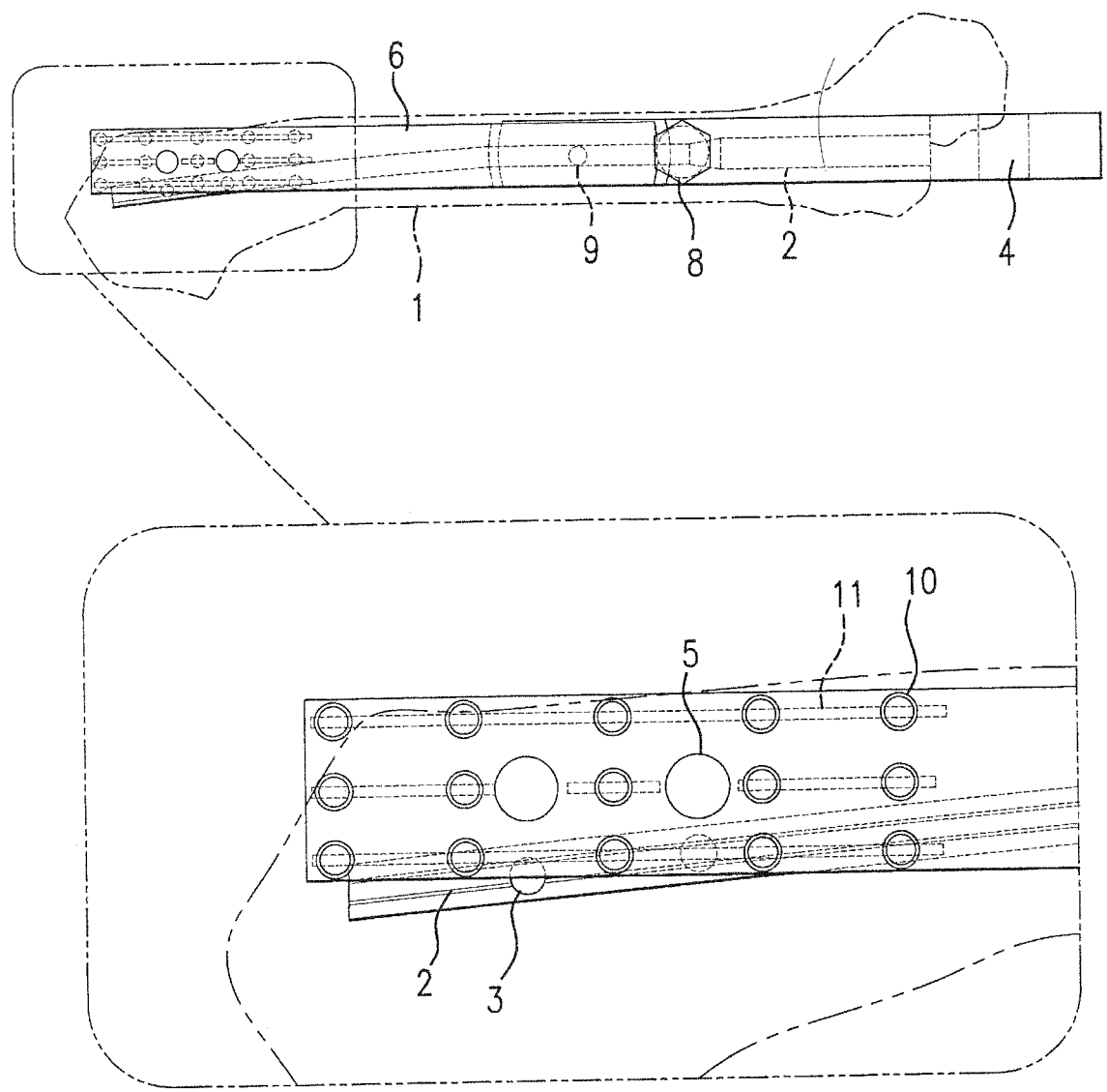
FIG. 4 shows a side view of an aiming arm according to a preferred embodiment of the present invention, wherein the fastened intramedullary nail is distorted after bone insertion, and wherein aiming arm holes and intramedullary nail transverse holes are not aligned thereof.

After implantation into the bone, the distortion of the intramedullary nail causes the intramedullary nail holes 3 to move out of alignment with aiming arm holes 5 as shown in FIG. 4.

Figure 6:
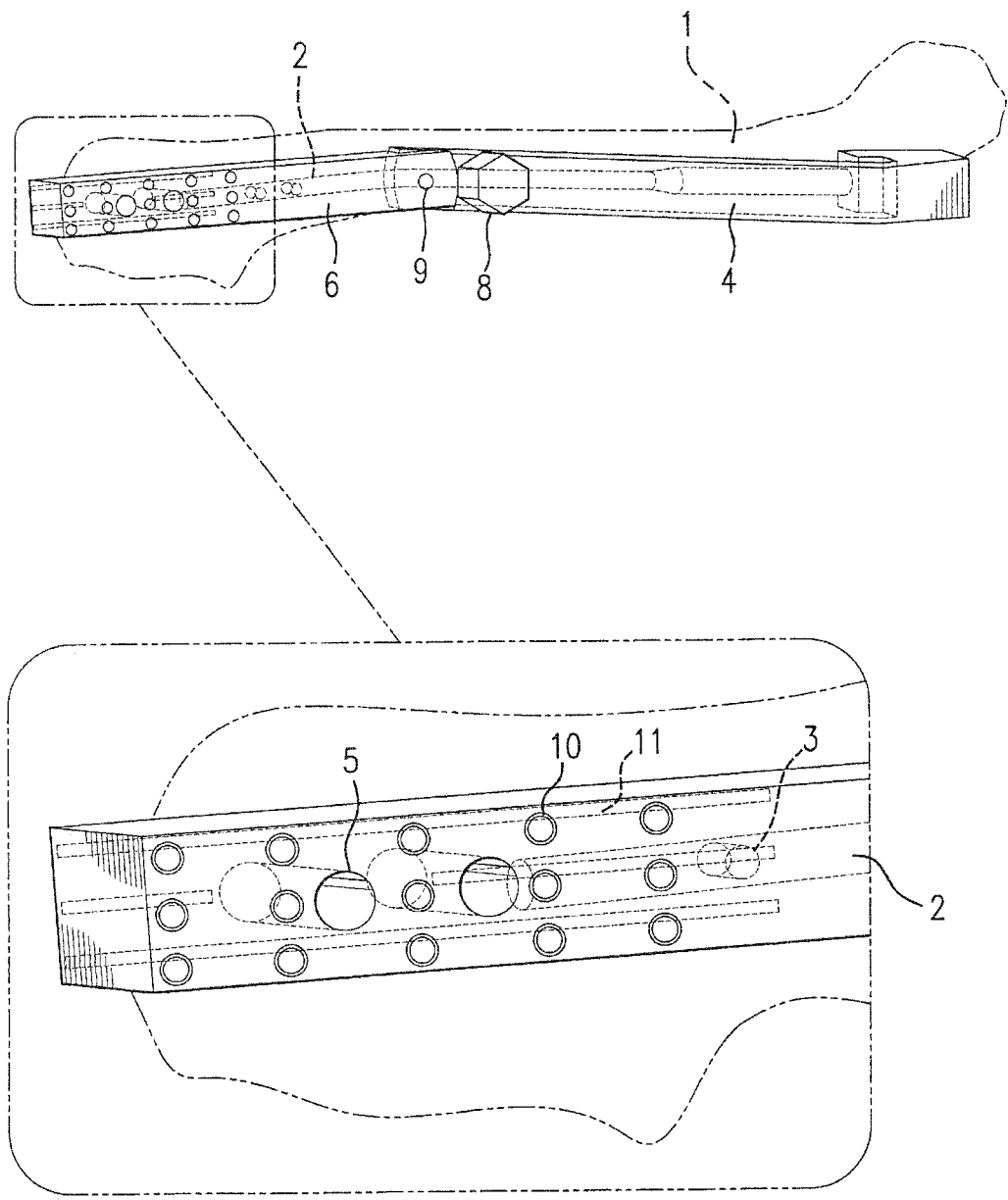
FIG. 6 is a perspective view in the plane of the aiming arm holes, illustrating how the alignment of intramedullary nail cross holes and aiming arm holes can be confirmed despite the fact that the X-ray beam is not aligned with the axis of the intramedullary nail holes.

In a preferred embodiment, the aiming arm 4 is formed, at least partially, of a relatively radiolucent material and is provided with radiopaque target markers 10, 11, which enable one to asses when the position of the X ray source and ensure that the X-ray beam is coplanar with the plane of the aiming arm holes, eliminating the need for the X-ray beam to be coaxial with the intramedullary nail holes 3. As a consequence, a single snapshot from an X-ray source positioned such that an X-ray beam is coplanar with the aiming arm holes 5 is enough to determine the exact distortion of the intramedullary nail 2, as shown in FIG. 6.

Figure 5:
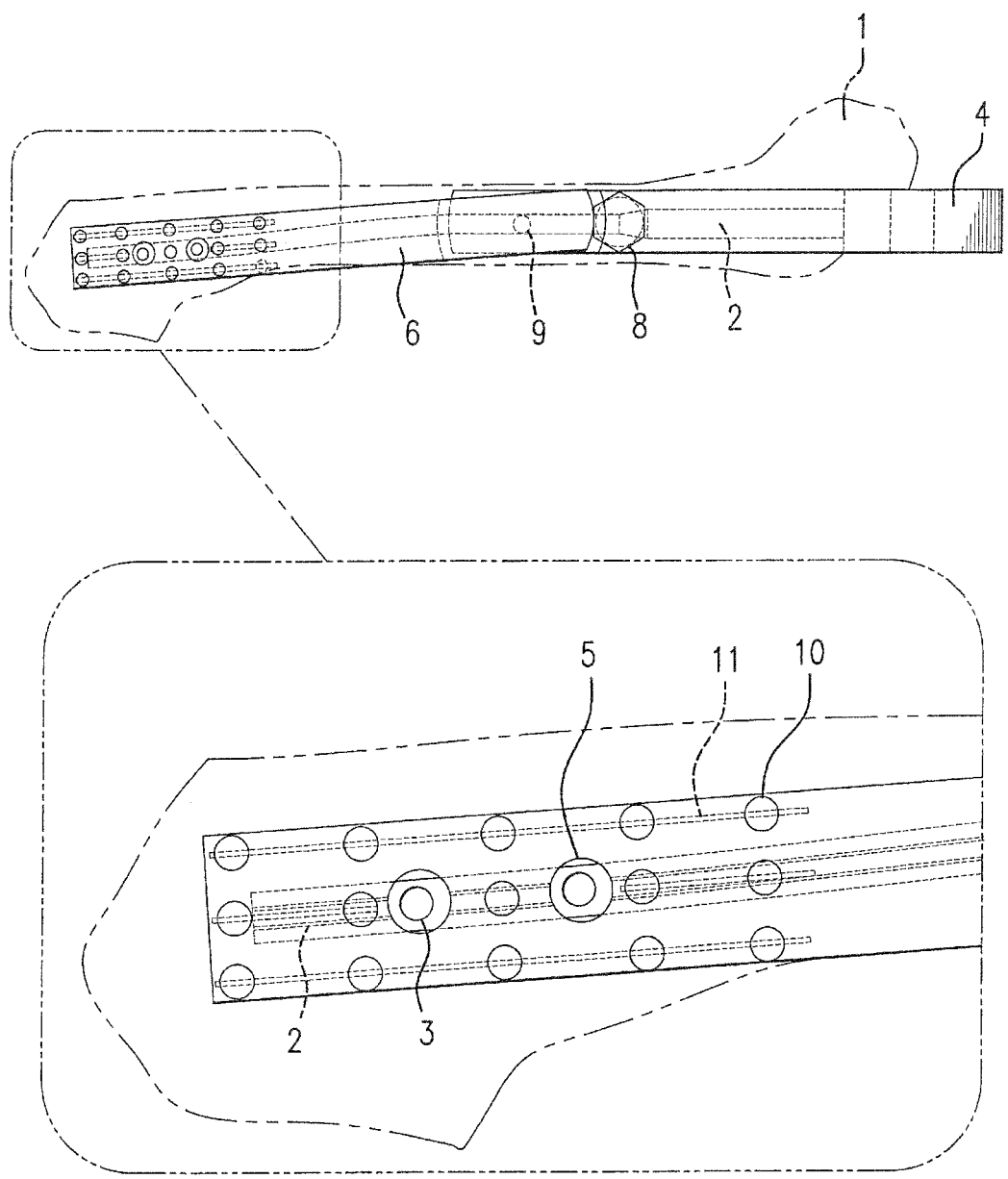
FIG. 5 shows a side view of an aiming arm according to a preferred embodiment of the present invention after compensation for the nail deformation was made, so that aiming arm holes and intramedullary nail transverse holes are aligned.
Figure 7:
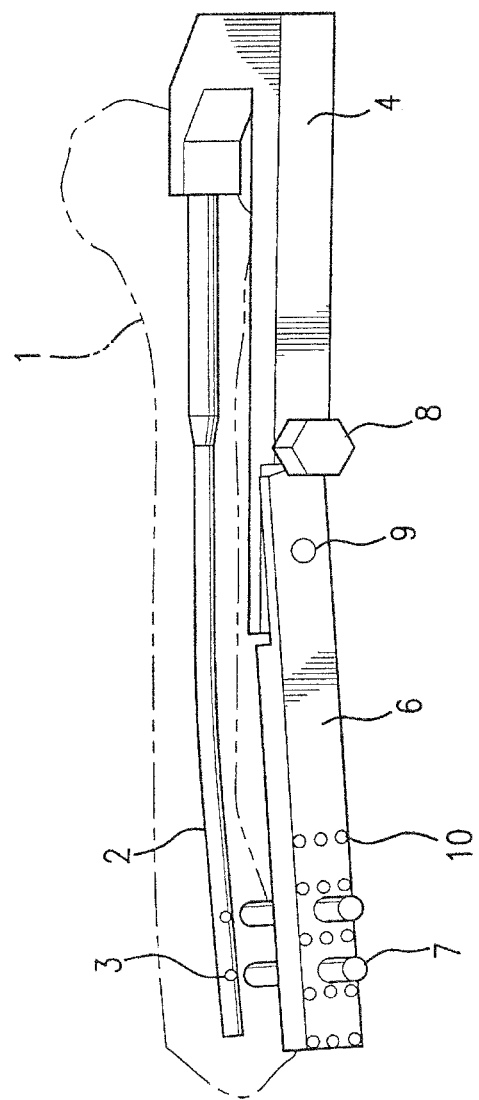
FIG. 7 shows a perspective view of FIG. 5.

By turning the adjusting knob 8 the required amount, the mobile part of the aiming arm 6 can be positioned to compensate for the distortion of the intramedullary nail 2, so that aiming arm holes 5 and nail holes 3 are re-aligned as shown in FIGS. 5 and 7.

Once aiming arm holes 5 and intramedullary nail holes 3 are aligned it is easy to slide in the protective sleeves 7 through the aiming arm holes 5. After the protective sleeves 7 are positioned, a drill bit is aligned with the nail hole 3 and drilled through the nail hole 3 and the surrounding bone material. Once the second drill bit is drilled accurately through the second nail hole 3 and the surrounding bone material, the second drill bit is removed, and a locking screw is inserted through the protection sleeve and screwed through the bone and second nail hole 3 to secure the nail to the bone. Finally, the first drill bit is removed, and a second locking screw is inserted through the sleeve 7 and screwed through the bone 1 and first nail hole 3 to secure the intramedullary nail 2 to the bone 1.

Next, an aiming arm device according to another preferred embodiment of the present invention will be explained with reference to FIGS. 8-14.

Figure 8:
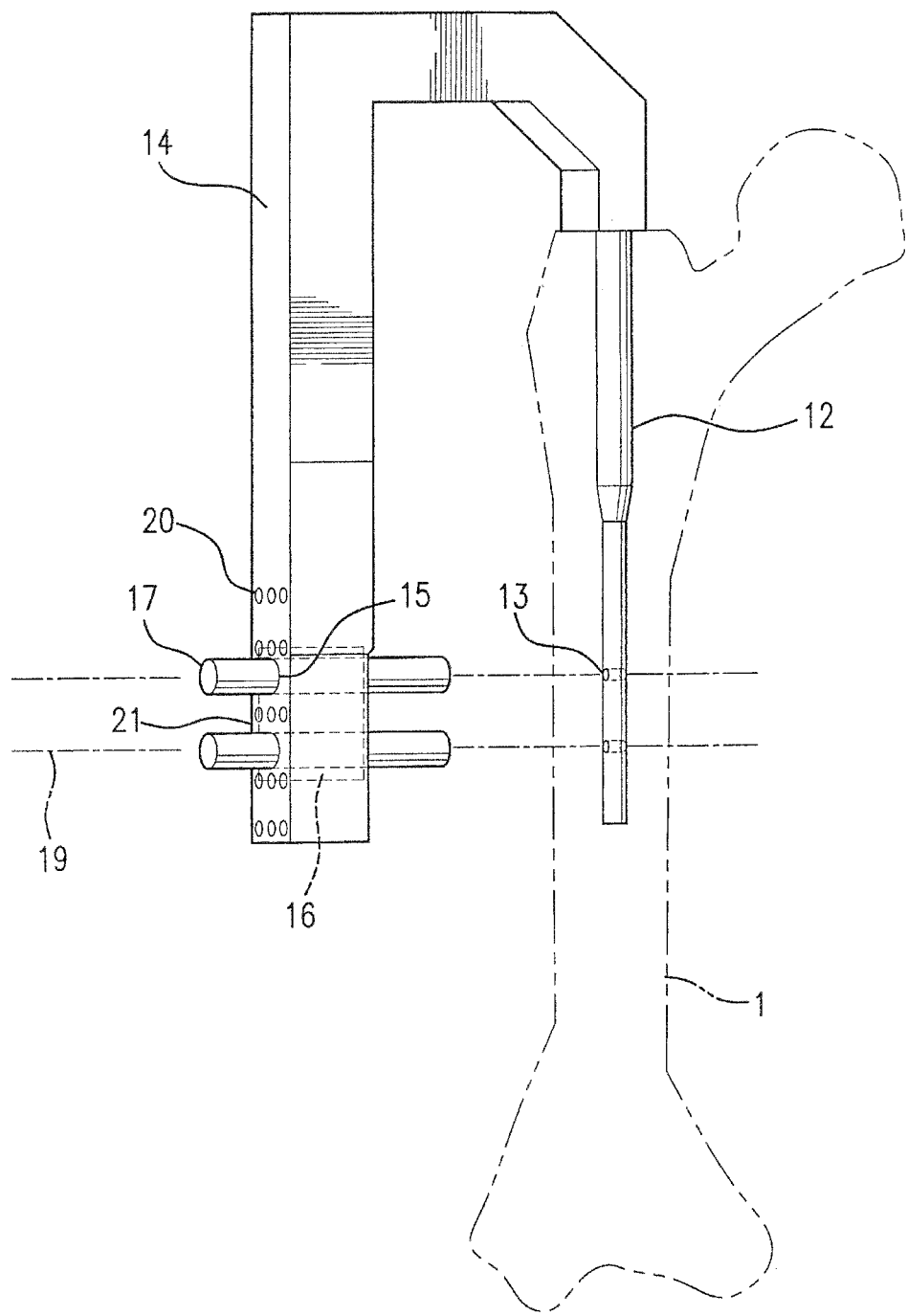
FIG. 8 shows a perspective view of an aiming arm according to a preferred embodiment of the present invention wherein a fastened short intramedullary nail implanted into the bone is shown.
Figure 9:
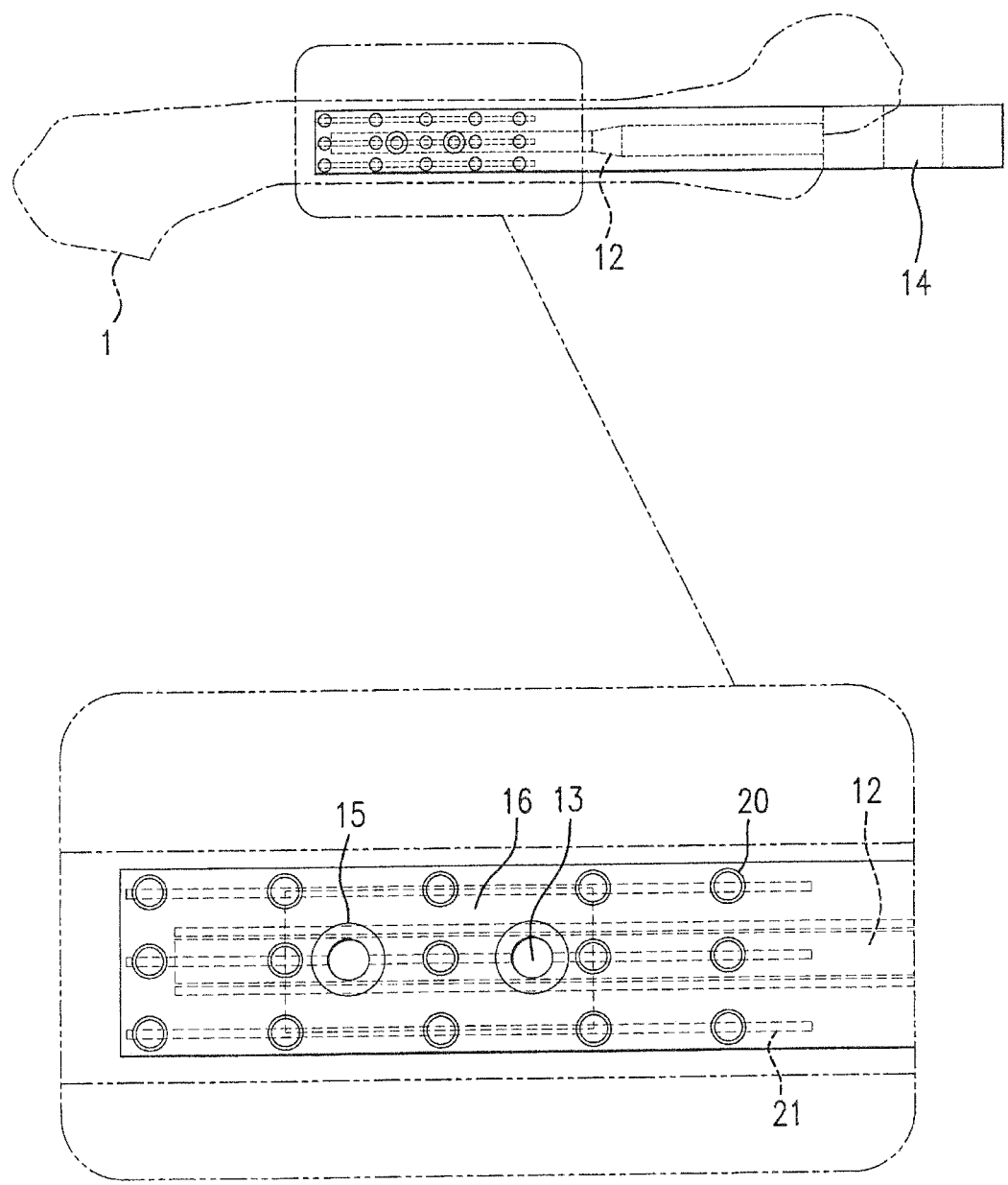
FIG. 9 is a side view illustrating the aiming arm holes precisely aligned with the short intramedullary nail.
Figure 10:
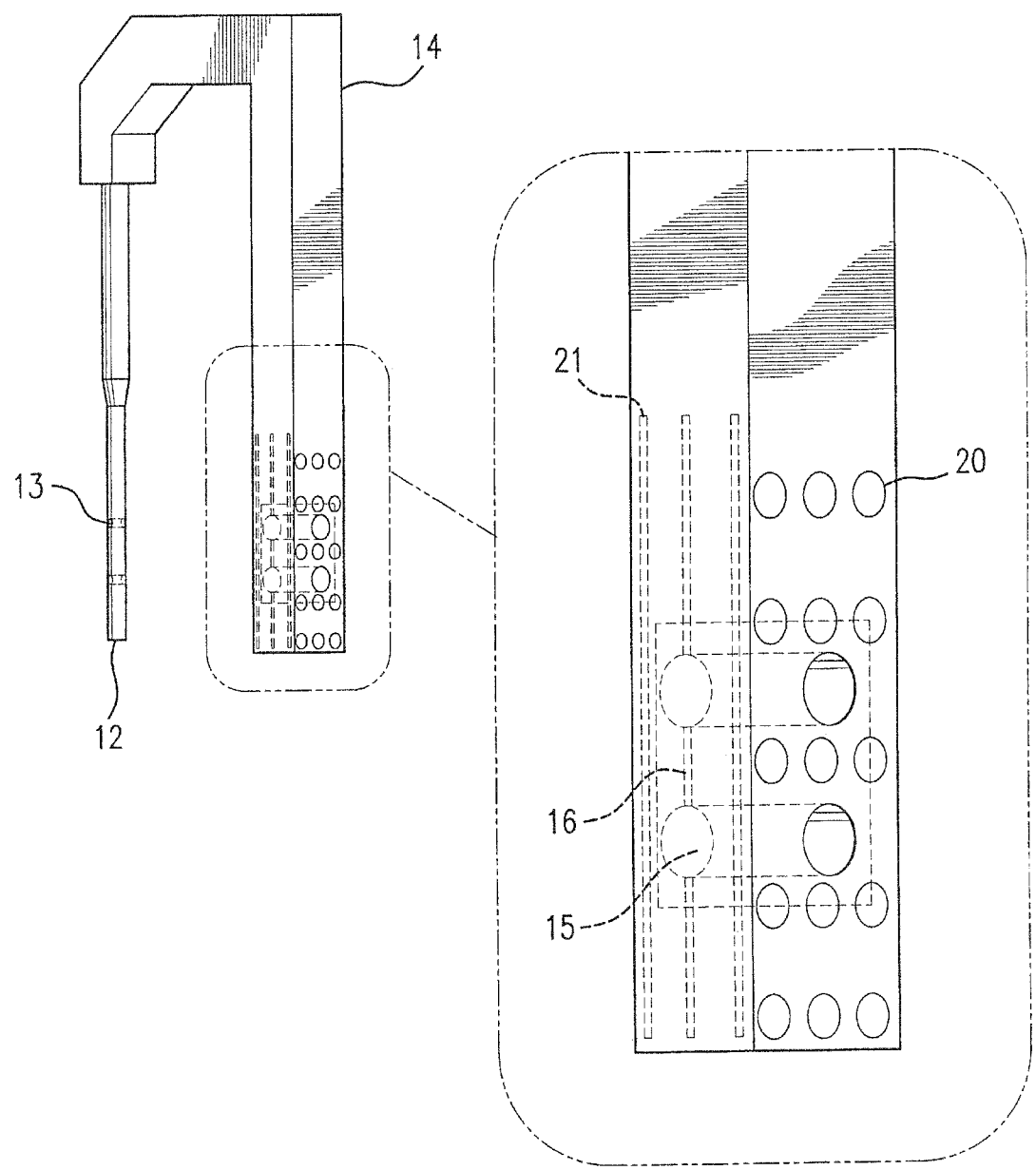
FIG. 10 shows a perspective view of FIG. 9, wherein the protective sleeves, the short intramedullary nail fastened to the aiming arm, and the front and rear radiopaque markers are shown.

Referring to FIG. 8 there is shown an aiming device 14, fastened to a short intramedullary nail 12. The intramedullary nail 12 is provided with two coplanar transverse holes 13. Protective sleeves 17 can slide through holes 15, existing in the insert 16 situated in the aiming arm 14 in order to guide drills and bone screws through the nail cross holes 13, for distal locking of the intramedullary nail 12. Insert holes 15, and nail holes 13 have the same axis 19.

The aiming arm 14 having radiopaque target markers, e.g., bubbles 20 and lines 21, is fastened to the bone nail 12. Before the intramedullary nail 12 is inserted into bone 1, aiming arm holes 15 and nail holes 13 are perfectly aligned as it can be seen in FIGS. 9 and 10.

Figure 11:
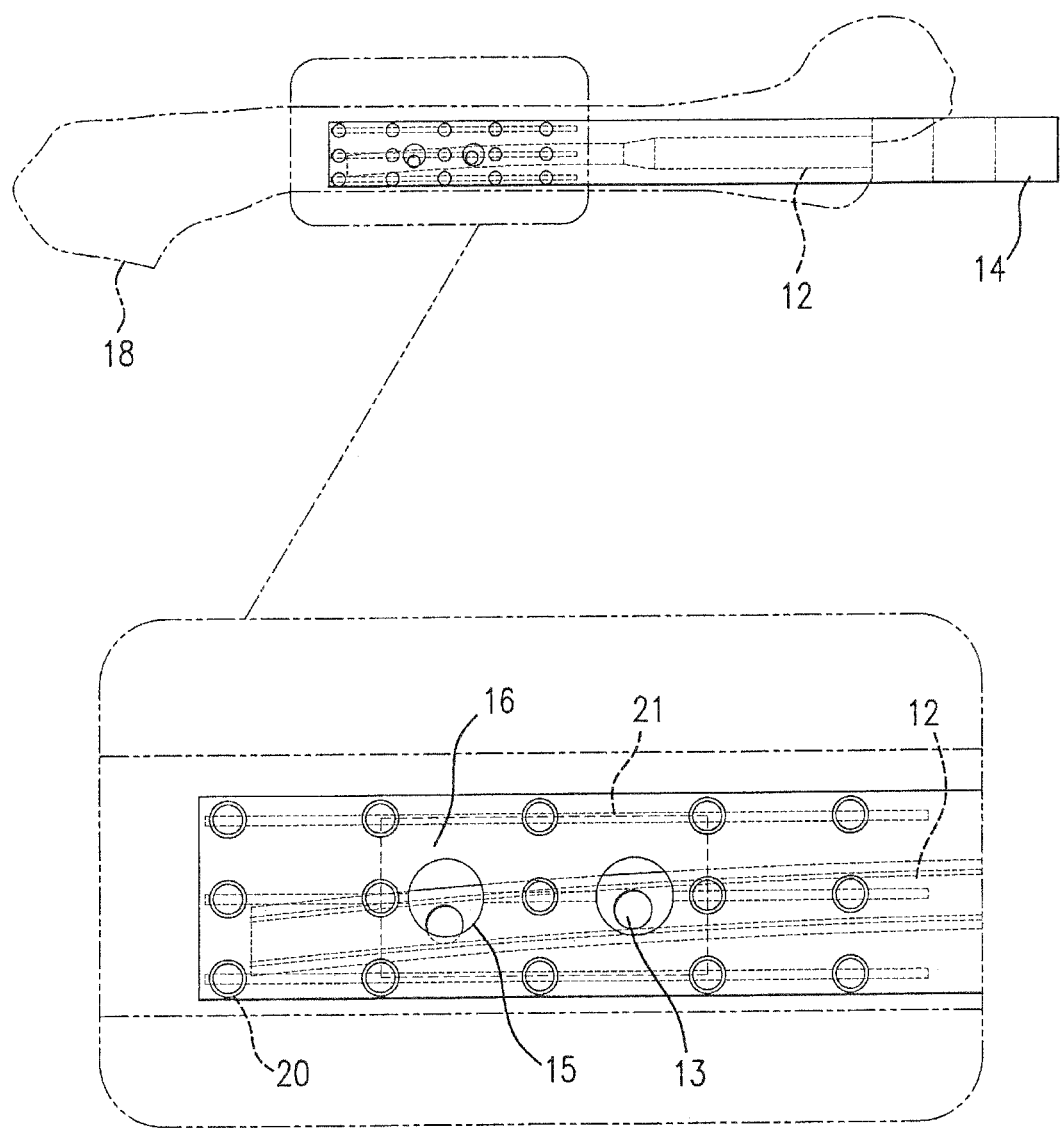
FIG. 11 shows a side view of the aiming arm according to a preferred embodiment of the present invention, wherein the fastened intramedullary nail is distorted after bone insertion, and wherein the aiming arm holes and intramedullary nail transverse holes are not aligned.

After insertion into the bone, the intramedullary nail 12 commonly distorts such that aiming arm holes 15 and nail holes 13 are not aligned anymore as shown in FIG. 11.

Figure 12:
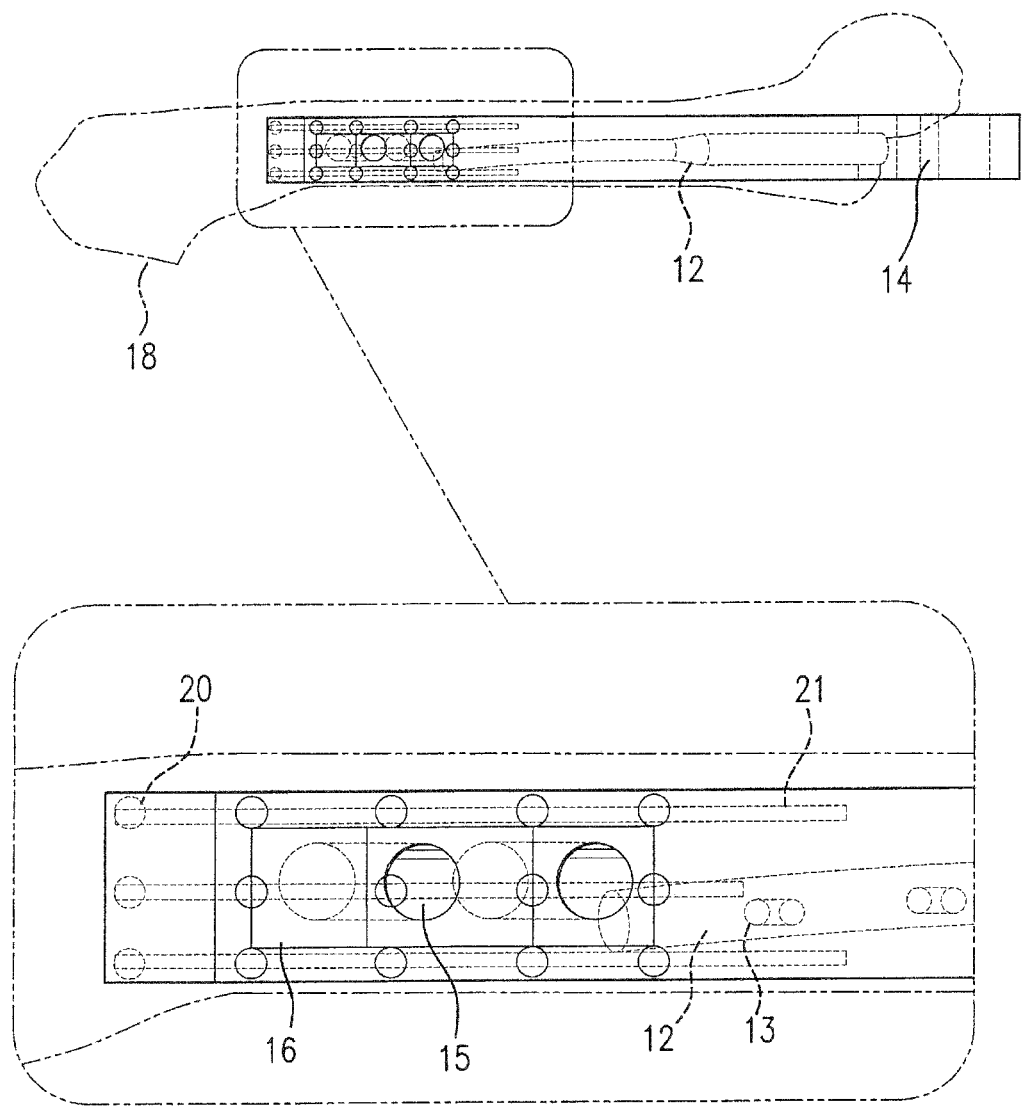
FIG. 12 is a perspective view in the plane of the aiming arm holes, illustrating how a single X-ray snapshot in this plane enables one to assess the exact distortion of the intramedullary nail after insertion into the bone.
Figure 13:
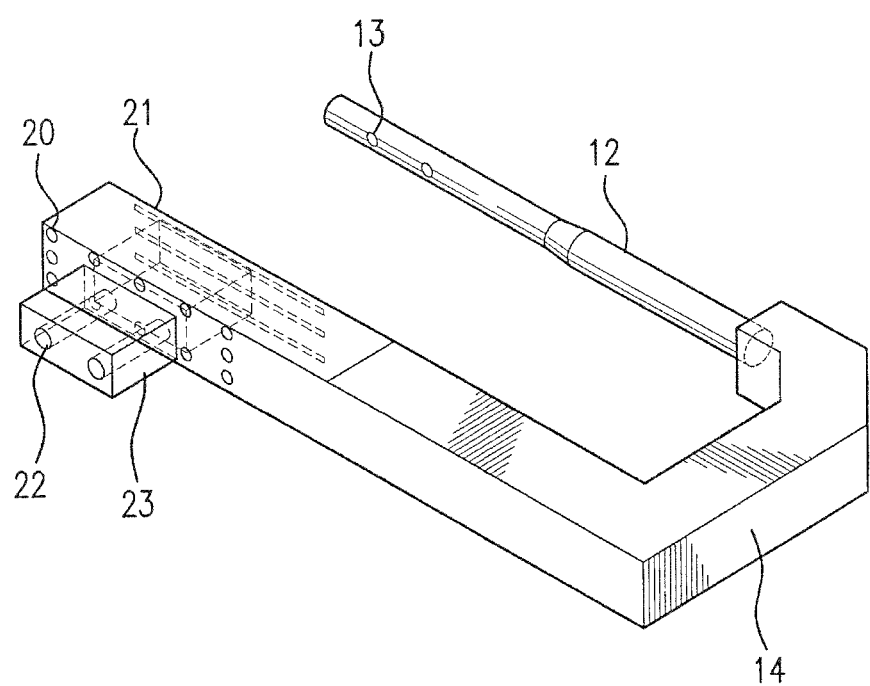
FIG. 13 shows a perspective view of the aiming arm according to a preferred embodiment of the present invention wherein the distorted intramedullary nail, and an insert with offset holes to compensate for the distortion of the intramedullary nail are shown.
Figure 14:
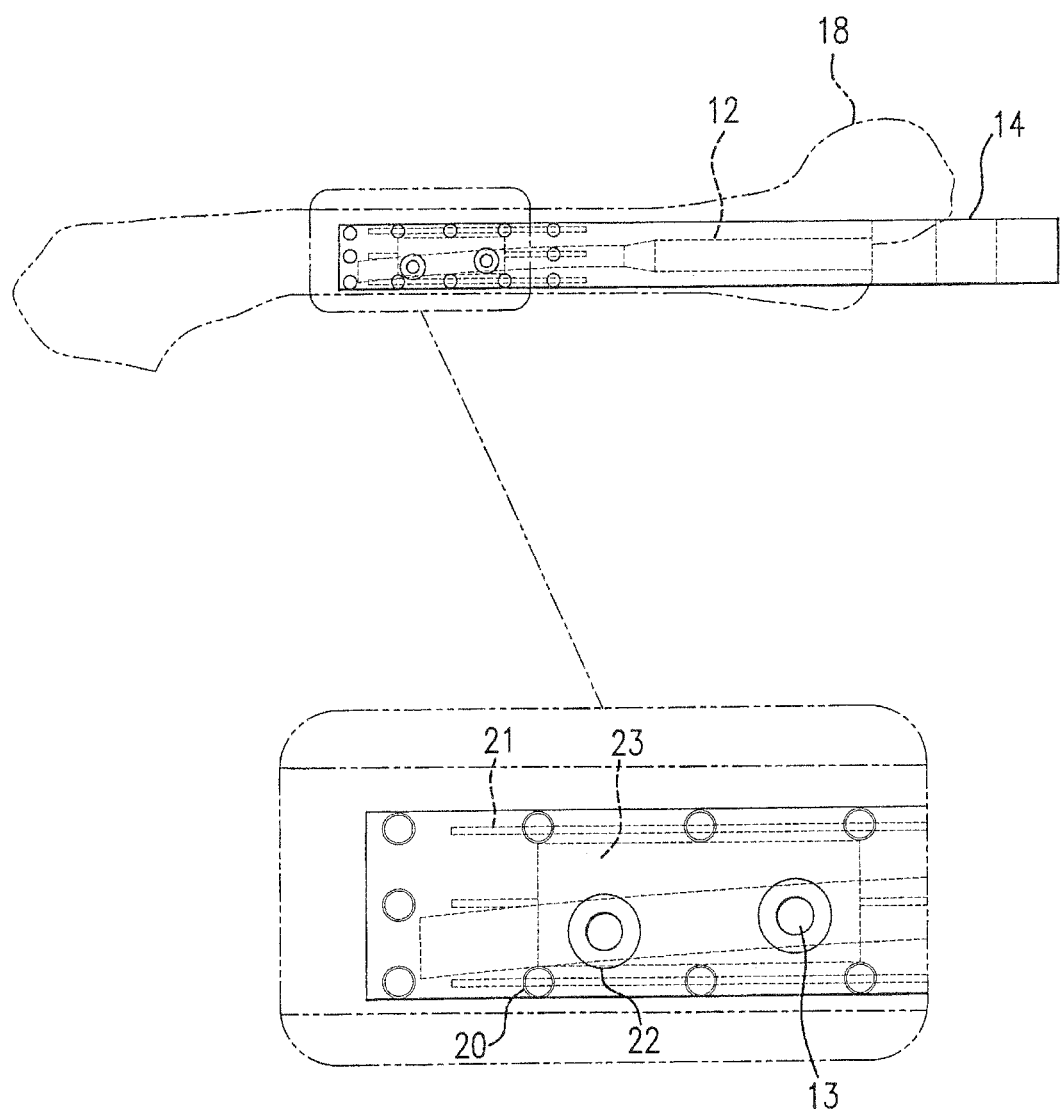
FIG. 14 shows a side view of FIG. 13.

A single snapshot of an X-ray source positioned such that an X ray beam is coplanar with the aiming arm holes 15 is sufficient to determine the amount of nail distortion, as shown in FIG. 12. By using an insert 16, provided with offset holes, aiming arm holes 15 and intramedullary nail holes 13 can be aligned again as shown in FIGS. 13 and 14.

Once aiming arm holes 15 and intramedullary nail holes 13 are aligned it is easy to slide in the protective sleeves 17 through the aiming arm holes 15 and slide a drill through the protective sleeves 17 to bore the bone 1. One may then slide bone screws through the protective sleeves 17 and through the aligned nail holes 13 in order to lock the intramedullary nail 12.

Figure 15:
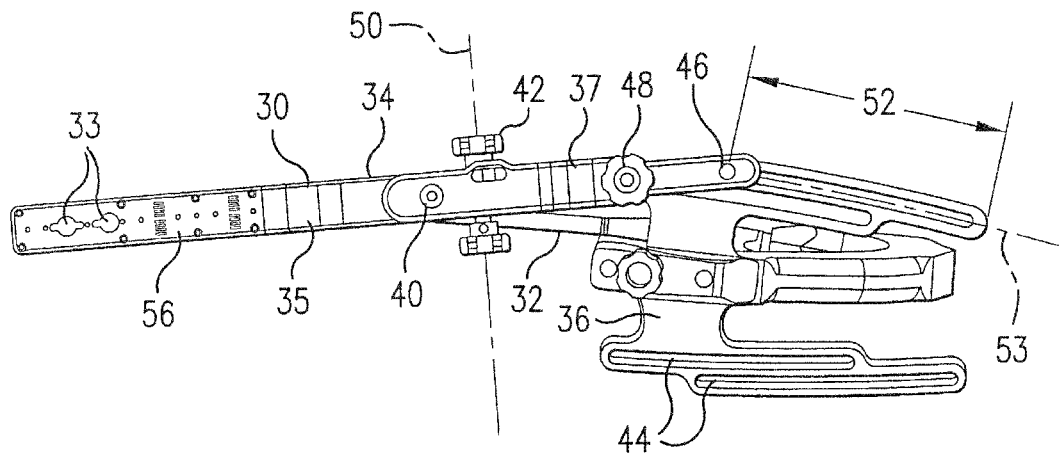
FIG. 15 is a side view of an aiming arm according to another preferred embodiment of the present invention, wherein the aiming arm is connected to an intramedullary nail.
Figure 16:
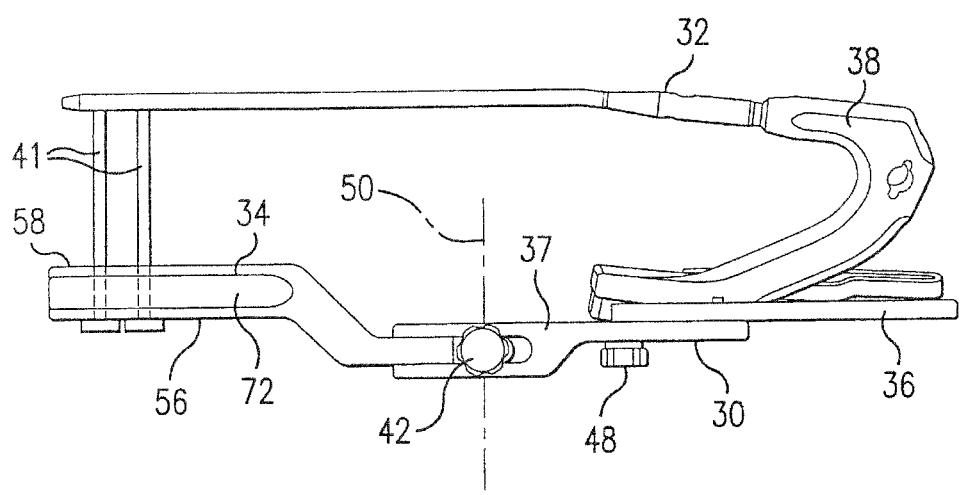
FIG. 16 is a top view of the aiming arm shown in FIG. 15.

In still another preferred embodiment, shown in FIGS. 15-16, the present inventions relates to a radiolucent aiming device 30 for targeting transverse bores in an intramedullary nail 32 in order to distally lock nail 32 in place within a patient's bone. Aiming device 30 includes an aiming arm 34, which is removably and adjustably connected to an upper handle 36 and includes at least one transverse hole 33 for receiving and guiding drilling and fixation elements. Aiming arm 34 is configured to be both rotated with respect to handle 36 about axis 50 and translated with respect to handle 36 along axis 53 in the direction 52. Aiming arm 34 may also be removed from and re-connected to handle 36 for use with either left-hand or right-hand intramedullary nails. Handle 36 is attached to intramedullary nail 32 via nail insertion handle 38, which is releasably mounted to aiming arm handle 36 via a bolt, screw or other connection element having a knurled nut 39.

Aiming arm 34 includes a radiolucent lower portion 35 and an upper portion 37, where lower portion 35 is pivotally attached to upper portion 37 via a pin 40 and includes an adjustment knob 42 that actuates a screw mechanism to rotate arm portion 34 about axis 50 in order to adjust the angle of lower aiming arm portion 35 with respect to upper aiming arm portion 37 and handle 36. In a preferred embodiment, axis 50 is parallel to the axis of the transverse holes in the intramedullary nail. Handle 36 also includes a plurality of elongated slots 44 along which the upper portion 37 of aiming arm 34 may be adjustably mounted. A particular rail is selected based upon the orientation of the nail, i.e., right or left, and the size/length of the nail 32. Once mounted along a slot 44 by one or more pins 46, aiming arm 34 may be releasably locked against further translation along the direction 52 by knurled nut 48.

Figure 18:
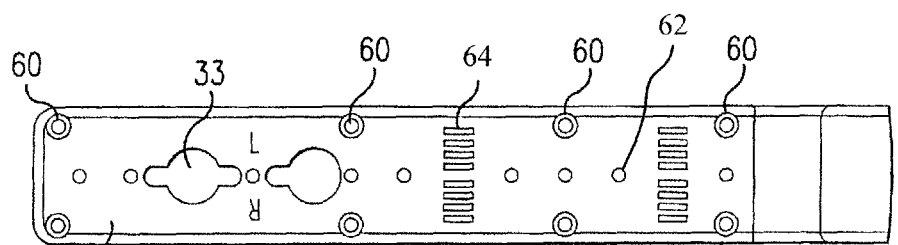
FIG. 18 is a partial view of a top surface of the distal portion of the aiming arm of FIG. 15 showing the radiopaque markers.
Figure 19:
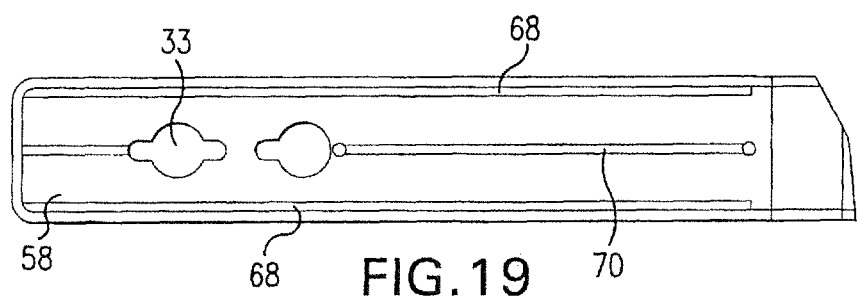
FIG. 19 is a partial view of the bottom surface of the aiming arm of FIG. 15, opposite the surface shown in FIG. 18.

As shown best in FIGS. 18 and 19, lower portion 35 of aiming arm 34 includes a set of radiopaque markers on both its top and bottom surfaces, 56, 58, respectively. Top surface 56 includes a plurality of peripheral circles 60 aligned along the two longitudinal edges of top surface 56 and a series of dots 62 along the centerline of top surface 56. In addition, as discussed more fully below, a series of scale markers 64 (in the form of dashes), aid in determining the degree of angular adjustment necessary when the aiming arm 34 is not correctly aligned with the X-ray source. Top surface 56 may also include radiopaque markers 66 indicating the correct orientation of the device for the given installation, i.e., the letters "L" and "R." In a preferred embodiment, circles 60 may have a diameter on the order 5.0 mm and scale markers 64 may have a length on the order of 5.0 mm.

Figure 17:
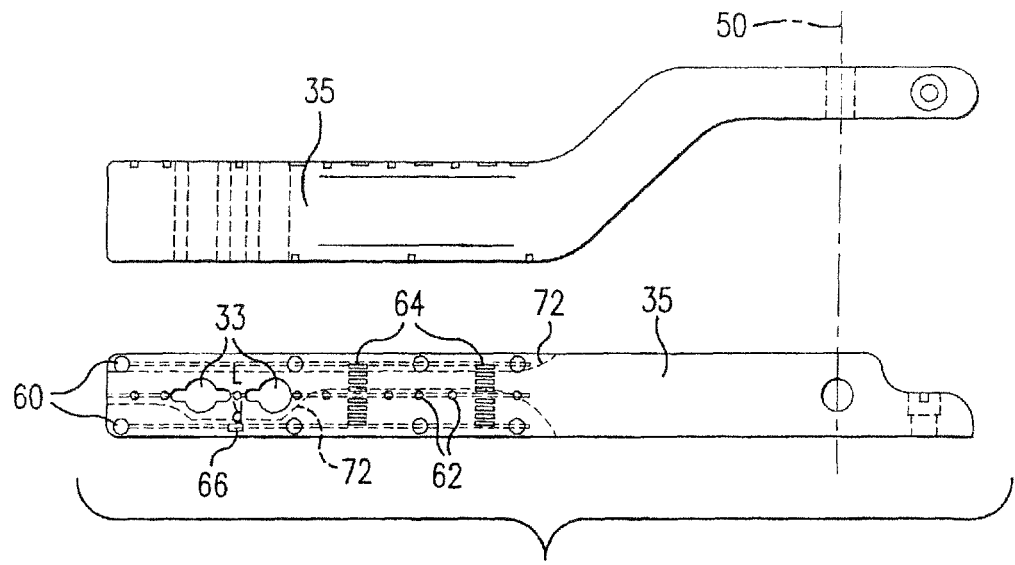
FIG. 17 includes both top and side views of the lower portion of the aiming arm of FIG. 15.

As shown in FIG. 19, bottom surface includes its own set of radiopaque markers in the form of two peripheral lines 68 and one median line 70, all of which run parallel to one another. Peripheral lines 68 extend along both longitudinal edges of the bottom surface 58, while median line 70 runs along the centerline of bottom surface 58. Lines 68, 70 may a have a thickness on the order of 1.0-2.0 mm. As shown in FIGS. 16 and 17, in addition to being radiolucent, lower portion 35 of aiming arm 34 may include one or more recessed sections 72 between the top and bottom surfaces 56, 58, and their respective sets of radiopaque markers, such that less solid material lies between the radiopaque markers. This will aid in visualization and alignment of the radiopaque markers under image intensification.

In an effort to further describe the features and benefits of the present invention, reference will now be made to a method of using the disclosed aiming device. First, prior to insertion of the intramedullary nail, the nail must be properly aligned with the aiming device of the present invention.

Accordingly, nail insertion handle 38 is attached to aiming arm handle 36. Next, aiming arm 34 is connected to an appropriate slot 44, which is selected based upon the nail length/size and the side of the patient requiring implantation, i.e., left or right. Knurled nut 48 is loosely coupled to handle 36 and calibration trocars 41 are used to align the aiming arm holes 33 with the transverse holes in the intramedullary nail and determine the appropriate length of aiming arm 34. Once the aiming arm holes 33 are properly aligned with the nail holes, knurled nut 48 is tightened securely and the calibration trocars are removed from device 30. Following this initial calibration, aiming device 30 is removed from insertion handle 38, and the nail is inserted into the medullary canal of the patient. After insertion, the nail is typically locked proximally using known techniques.

Figure 20:
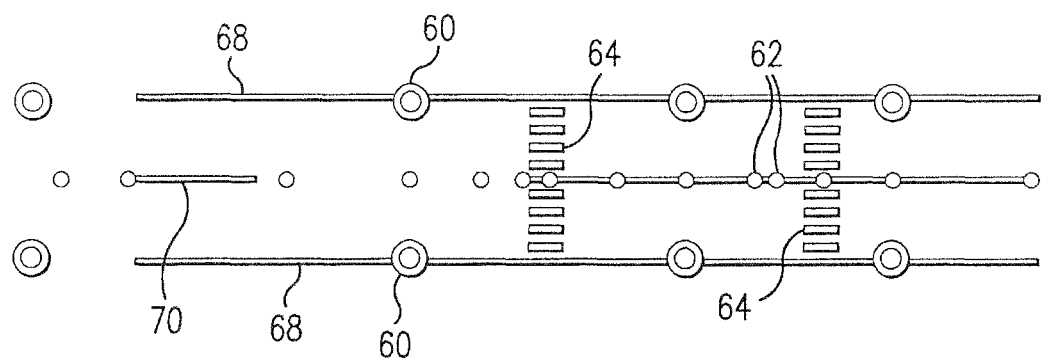
FIG. 20 is a partial view of the properly aligned radiopaque markers of the aiming arm shown in FIG. 15.

With the nail 32 inserted into the patient and proximally locked, aiming device 30 is re-attached to the nail insertion handle 38, with care taken not to adjust the knurled nut 48, which locks the aiming arm 34 against translational movement along slot 44. Next, the image intensification equipment (C-ARM) is moved toward the patient and angled approximately 30-40° to the longitudinal axis of the bone. (This keeps the surgeon out of the radiation beam and helps avoid the contralateral limb.) Next, using the C-ARM, the surgeon verifies that the image of the radiopaque markers of aiming arm 34 is configured for the appropriate side (left or right). If so, the "L" or "R" symbol, shown as 66 in FIG. 17. If necessary, the image may be transposed. While still using the C-ARM, the surgeon then identifies the various radiopaque markers, e.g., peripheral circles 60, dots 62, scale markers 64, and lines 68, 70. The C-ARM beam is then adjusted in order to align the dots 62 so that they overlay the median line 70 and/or so that the relationship between the peripheral circles 60 and peripheral lines 68 is symmetrical (as shown in FIGS. 5 & 20). Therefore, if the dots 62 and circles 60 are above lines 68 and 70, the C-ARM should be rotated down, and if the dots 62 and circles 60 are below the lines 68, 70, then the C-ARM should be rotated up. In a preferred embodiment, scale markers 64 are configured such that each graduation of the scale represents 2° of rotation. Therefore, the surgeon can use the scale markers 64 to determine the amount the C-ARM needs to be rotated in order to properly align the beam with the plane of the aiming arm holes 33. As shown in FIG. 20, when the center dots 62 overlay the median line 70, and the peripheral circles 60 lie symmetrically with respect to the peripheral lines 68, aiming arm 34 has been properly aligned with the C-ARM. If circles 60 are not symmetrically positioned with respect to the peripheral lines 68, the C-ARM still requires adjustment.

Once aiming arm 34 is properly aligned with the C-ARM, the surgeon can visualize the nail and determine if any deflection in the anterior-posterior plane, i.e., in a direction perpendicular to the axis of the nail holes, has occurred. If so, the lower portion 35 of aiming arm 34 can be adjusted to re-align the aiming arm holes 33 with the nail holes. As discussed above, turning of adjustment knob 42 rotates the lower portion 35 of aiming arm 34 with respect to the handle 36 to accomplish this alignment and compensate for the anterior-posterior nail deflection. After adjusting the angle of the aiming arm 34, a final check should be made to ensure that the radiopaque markers are still in proper alignment. If not, the alignment steps described above should be repeated. Once aligned, a sleeve/trocar assembly is inserted through the aiming arm holes 33, and the radiopaque markers are checked once again to confirm alignment prior to drilling and insertion of locking elements.

While I have illustrated and described preferred embodiments of the invention, it will be understood that those skilled in the art will thereby be enabled to devise variations and modifications without departing from the spirit and scope of this invention, which is defined only by the following claims.

What is claimed is:

1. A method for locating holes for distal locking of an implanted intramedullary nail, comprising the steps of:
    implanting into a bone an intramedullary nail having a proximal end, a distal end, and a distal locking hole;
    connecting to the proximal end of the intramedullary nail an aiming device, an aiming arm of the aiming device being formed of a radiolucent material, the aiming arm having a transverse hole extending therethrough from a first surface of the aiming arm to a second surface thereof, the first surface including a first radiopaque marker and the second surface including a second radiopaque marker, the first radiopaque marker comprising a plurality of circles and the second radiopaque marker comprising a line;
    adjusting a position of an X ray source until the first and second markers are aligned in a predetermined orientation relative to one another, the first and second markers being positioned relative to one another such that, when the first and second markers are aligned in the predetermined orientation, X rays from the X ray source are emitted in a beam coplanar with a central axis of the aiming arm transverse hole; and
    rotating the aiming arm until the distal locking hole aligns with the transverse hole of the aiming arm in an image generated by the X rays from the Xray source.

2. The method of claim 1, further comprising the steps of:
    connecting the aiming device to the intramedullary nail before the nail is implanted in a patient; and
    adjusting the position of the aiming arm relative to the intramedullary nail using an elongated slot formed in a handle portion to align the transverse hole of the aiming arm with the distal locking hole.

3. The method of claim 1, wherein the second radiopaque marker is scaled to indicate an adjustment value to a user.

4. The method of claim 1, wherein the first and second radiopaque markers are configured to indicate alignment of the X-ray source to facilitate alignment of the X-ray beam so that it is coplanar with the central axis of the transverse hole of the aiming arm.

5. The method of claim 1, wherein alignment of the radiopaque markers on the first and second surfaces indicates that the X-ray beam is coplanar with a plane defined by the central axis of the aiming arm transverse hole and a position of a longitudinal axis of the intramedullary nail, before the intramedullary nail was inserted into the bone.

6. The method of claim 1, further comprising the step of adjustably rotating the aiming arm about an offset axis parallel to the central axis of the transverse hole of the aiming arm.

7. The method of claim 1, further comprising the step of turning an adjusting knob on the aiming arm, the adjusting knob configured to rotate the aiming arm relative to the intramedullary nail to which it is coupled.

8. The method of claim 7, wherein a proximal portion of the aiming arm remains stationary while a distal portion thereof is mobile, the distal portion of the aiming arm being positionable via the adjusting knob.

9. The method of claim 1, wherein the aiming arm is configured to rotate about an axis transverse to a longitudinal axis of the aiming arm.

10. A method for locating holes for distal locking of an implanted intramedullary nail, comprising the steps of:
- implanting into a bone an intramedullary nail having a proximal end, a distal end, and a distal locking hole;
- attaching a handle portion of an aiming device to the intramedullary nail, the aiming device including an aiming arm formed of a radiolucent material and having a transverse hole extending therethrough between first and second surfaces thereof, the first surface including a first radiopaque marker and the second surface including a second radiopaque marker, the first and second radiopaque markers being positioned along the first and second surfaces;
- positioning an imaging device so that the first and second radiopaque markers symmetrically overlay one another, the first and second radiopaque markers being positioned so that, when they appear in this position, an imaging beam of the imaging device is coplanar with a central axis of the transverse hole of the aiming arm, wherein the first and second radiopaque markers are configured so that, when asymmetrically overlaying one another they indicate a direction and an amount by which the aiming arm must be rotated to align the imaging beam with a plane of the central axis of the transverse hole of the aiming arm; and
- based on imaging device data, rotating the aiming arm relative to the handle portion to align the aiming arm transverse hole with the distal locking hole.

11. The method of claim 10, wherein the imaging device is an X-ray source.

12. The method of claim 10, wherein the aiming arm is configured to rotate about an axis transverse to a longitudinal axis of the aiming arm.

13. The method of claim 10, wherein the first radiopaque marker is longitudinally aligned with a plane including the transverse hole.

14. The method of claim 10, further comprising the step of taking an imaging device snapshot to determine a location of the distal locking hole of the implanted intramedullary nail relative to the transverse hole of the aiming arm.

15. The method of claim 10, further comprising the step of adjusting the position of the aiming arm relative to the intramedullary nail using an elongated slot formed in the handle portion to align the transverse hole of the aiming arm with the distal locking hole.

16. The method of claim 10, further comprising the step of turning an adjusting knob on the aiming arm, the adjusting knob configured to rotate the aiming arm relative to the intramedullary nail to which it is coupled.

17. The method of claim 16, wherein a proximal portion of the aiming arm remains stationary while a distal portion thereof is mobile, the distal portion of the aiming arm being positionable via the adjusting knob.

18. The method of claim 10, wherein the first radiopaque marker includes a plurality of circles.

19. The method of claim 10, wherein the second radiopaque marker includes a plurality of lines.

20. The method of claim 10, further comprising the step of determining an amount the aiming arm must be rotated via scale markers on the second surface, the scale markers comprising a plurality of gradations, each gradation representing 2 degrees of rotation such that when the first radiopaque marker is aligned with one of the plurality of gradations, the amount the aiming arm must be rotated can be determined.

* * * * *